United States Patent [19]

Damico

[11] Patent Number: 4,500,316
[45] Date of Patent: Feb. 19, 1985

[54] DISPOSABLE GARMENT

[75] Inventor: Joyce A. Damico, Winnebago County, Wis.

[73] Assignee: Kimberly-Clark Corporation, Neenah, Wis.

[21] Appl. No.: 500,120

[22] Filed: Jun. 1, 1983

[51] Int. Cl.³ ............................................. A61F 13/16
[52] U.S. Cl. ................................... 604/389; 604/385
[58] Field of Search ............... 604/358, 378, 379, 380, 604/381, 382, 383, 385, 389

[56] References Cited

U.S. PATENT DOCUMENTS

| 2,684,677 | 1/1953 | Pinney | 604/385 |
|---|---|---|---|
| 2,834,347 | 5/1958 | Connally . | |
| 3,150,663 | 9/1964 | Combs | 604/385 |
| 3,860,003 | 11/1973 | Buell . | |
| 4,034,752 | 3/1976 | Tritsch . | |
| 4,050,462 | 3/1976 | Woon et al. . | |
| 4,067,336 | 9/1976 | Johnson . | |
| 4,182,334 | 12/1977 | Johnson . | |
| 4,253,461 | 10/1979 | Strickland . | |
| 4,317,449 | 1/1980 | Nowakoski . | |
| 4,324,245 | 12/1979 | Mesek et al. . | |

FOREIGN PATENT DOCUMENTS

2080093 7/1981 United Kingdom .
2095561 3/1982 United Kingdom .

Primary Examiner—John D. Yasko
Assistant Examiner—Christa K. Scott
Attorney, Agent, or Firm—Paul A. Leipold; R. Jonathan Peters

[57] ABSTRACT

A disposable incontinent garment having a narrow crotch portion integrally connected to front and back body-encircling portions, with elastic leg bands extending along the longitudinal margins of the crotch and elastic waist bands extending along the latitudinal margins of the front and back portions, the elastic bands cooperating to form generally truncated triangular front and back pocket portions between relatively large convolutions along the legs and bases of the triangular pockets to provide increased containment and comfort features of the garment. A plurality of attachment tapes secure the front and back portions of the garment together in use and provide appropriate leg and waist band seals as well as supporting and stabilizing the front and back pocket portions.

20 Claims, 9 Drawing Figures

DISPOSABLE GARMENT

FIELD OF THE INVENTION

The present invention relates generally to disposable garments and more particularly concerns such disposable garments as incontinence briefs for absorbing and containing discharged body fluids and wastes.

BACKGROUND OF THE INVENTION

Although not widely discussed in the public literature, it has been recognized that there is an important need for disposable garments to absorb and contain body fluids and wastes of incontinent adults and ambulatory children. As used herein, such disposable garments are referred to as "incontinence briefs".

Due to the physical and sociological factors which are typical of the users of incontinence briefs, such products must meet even more stringent criteria than are normally imposed on disposable diapers for babies, infants or even toddlers. Generally speaking, incontinence briefs must be larger in size and have more absorptive and containment capacity than baby diapers. Also, older children and adults are more conscious of such factors as comfort, security and appearance, which are important physical and psychological considerations.

In the past, there have been attempts made to satisfy these rather conflicting requirements and, although some progress has been made, a wholly satisfactory solution has not previously been found. The following U.S. patents are representative of the art directly concerning adult incontinence garments: Johnson U.S. Pat. No. 4,182,334, which discloses a folded containment device that is upwardly concave in both the transverse and longitudinal directions; Strickland et al U.S. Pat. No. 4,253,461, which discloses an absorbent brief with elasticized leg portions and a special arrangement of attachment tapes intended to provide improved sealing around the thighs and waist of the user; and, Nowakoski U.S. Pat. No. 4,317,449, which discloses a "wing-folded" incontinence brief with self-storing attachment tapes intended to fit users of widely varying sizes. None of these devices, however, meet all of the requirements of fit, convenience, containment, comfort, absorbency, security and appearance that are desired in adult incontinence briefs.

As noted above, adult incontinence briefs, in some respects, are similar to disposable baby diapers and, in this regard, the following additional U.S. patents may be taken as representative: Buell U.S. Pat. No. 3,860,003, which discloses a disposable elastic leg diaper with flexible side flaps; Woon et al U.S. Pat. No. 4,050,462, which discloses an elastic leg diaper with gross transverse rugosities in the crotch area; Mesek et al U.S. Pat. No. 4,324,245, which discloses a disposable diaper with relatively wide constringent means in the leg opening and waist areas to form a plurality of macropleats in the side margins and pillow-like bulges in the absorbent batt; and, Ryan et al U.S. Pat. No. 4,326,528, which discloses an elastic legged diaper with a gathered crotch area bounded by flex regions and semi-rigid generally planar sides extending upwardly therefrom. While each of these patents provide diaper constructions with certain features and advantages, none of them disclose products that satisfy all of the characteristics desired in an adult incontinence brief.

OBJECTS OF THE INVENTION

Accordingly, it is an object of the invention to provide an improved incontinence brief or garment with integrally formed front and back pocket portions that considerably enhance the absorbency and containment capacity of the garment and also improve the comfort, security, appearance and convenience of the user.

It is a related object to provide a disposable incontinence garment that allows for intermittent inspection for wetness or soiling and partial removal to permit normal use of a toilet without unfastening the garment.

These and other objects and advantages of the invention will become more readily apparent upon reading the following Summary of the Invention taken in conjunction with the detailed description and the appended drawings.

SUMMARY OF THE INVENTION

According to the present invention, a disposable incontinence brief or garment for absorbing and containing body wastes includes a fluid pervious inner sheet, a fluid impervious outer sheet and a batt of absorbent material therebetween. The garment has a generally hour-glass shape with the relatively narrower crotch portion integral with the front and back portions which partially encircle the trunk portion of the body. The front or back portion is provided with securement means attached at the longitudinal marginal edge. The garment includes elastic leg bands or strips disposed longitudinally near or adjacent the marginal edges of the crotch portion and extending into the front and back portions of the garment. Elastic waist bands or strips extend transversely relative to the elastic leg bands across the front and back portions near or adjacent the latitudinal marginal edges thereof. Additionally, elastic leg bands and elastic waist bands are affixed to at least one of the inner and outer sheets of the garment. The elastic waist bands are enclosed outboard of the absorbent batt. In this manner, the elastic leg bands exert a longitudinal contracting and convoluting force in the crotch portion of the garment and the elastic waist bands exert a transverse contracting and convoluting force adjacent the ends of the front and back body-encircling portions of the garment. The contraction of the elastic leg bands and waist bands interact to form generally truncated triangular front and back pocket portions having one or more large longitudinally angled convolutions forming the legs of the triangular portions with the bases thereof located generally along the ends of the contracted and convoluted crotch portion of the garment.

In a preferred embodiment, the securement means includes a plurality of adhesive tapes attached to the back body-encircling portion with an upper tape on each side thereof extending laterally outwardly therefrom generally along and adjacent to an extension of the line of contracting force exerted by the back elastic waist band and with a lower tape extending laterally outwardly adjacent to or below a transverse line extending from the attached ends of the elastic leg bands located in the back portion. An intermediate tape is desirably disposed between the upper and lower tapes to seal and stabilize the mid-portion of the front and back portions of the garment and the front and back pockets formed therein.

DETAILED DESCRIPTION OF THE PREFERRED EMBODIMENT

Figure 1:
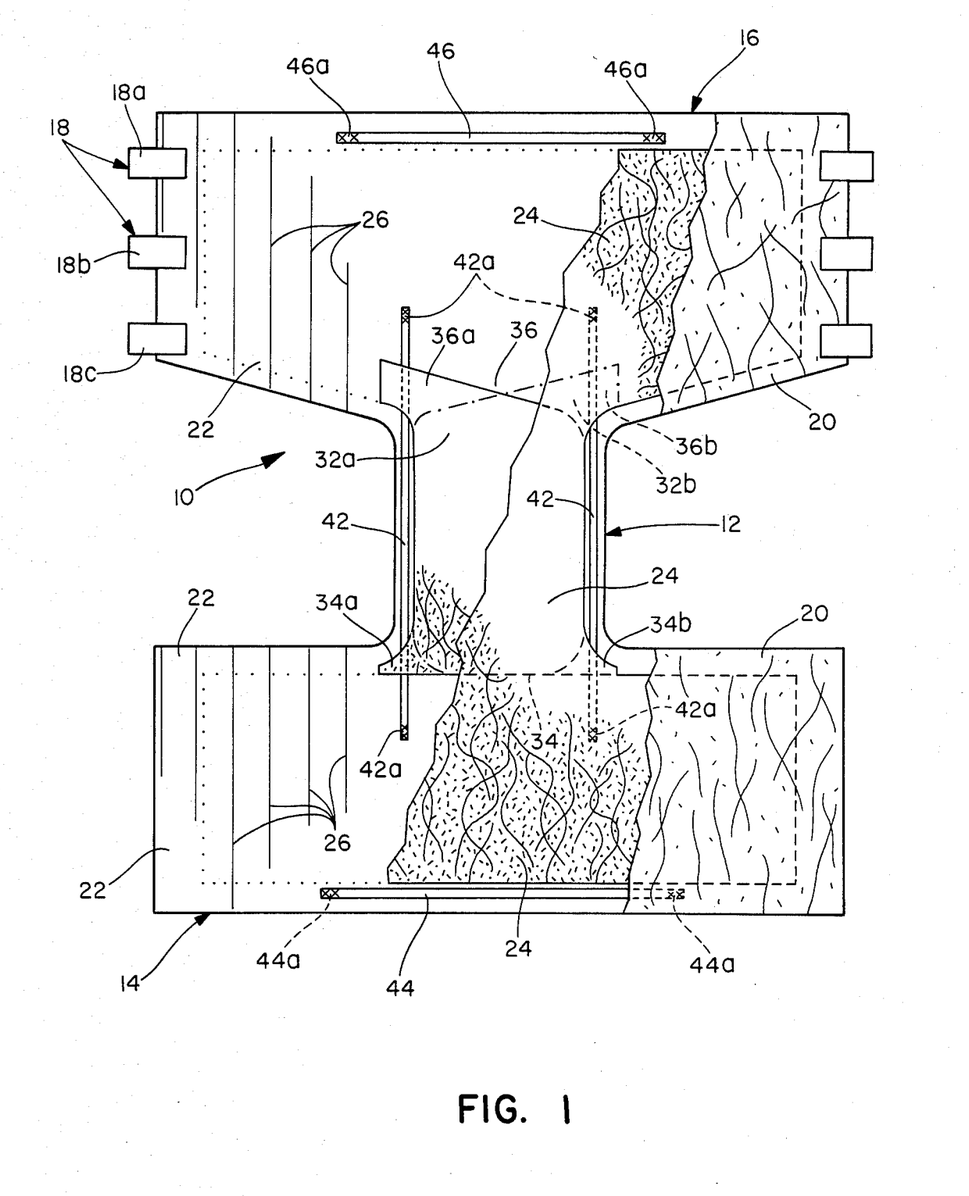
FIG. 1 is a top plan view of the disposable incontinence brief or garment of the present invention, in flat fully extended form, as viewed from the body side, with certain portions broken away to better illustrate the various layers and component elements of the garment.

Turning now to the drawings, there is shown in FIG. 1 a disposable garment 10 which embodies the features and advantages of the present invention. Generally speaking, such disposable garments are principally intended for use as absorbent incontinence briefs or disposable "adult diapers" for adults and ambulatory children, including toddlers, although such garments may also be useful for other purposes, without departing from the present invention.

As shown in the flat planar view of FIG. 1, the exemplary disposable garment 10 has a generally "Block I" or hour-glass shape with a narrowed crotch portion 12 along the longitudinal axis integrally connected to opposed front body-encircling portion 14 (front portion) and back body-encircling portion 16 (back portion). The front portion 14 is generally rectangular in shape with substantially latitudinal inner edges disposed transversely to said longitudinal axis and extending along the leg cut out areas from the opposed longitudinal sides of the garment 10 in toward the crotch portion 12. The latitudinal inner edges of the back portion 16 extend along the leg cut out areas inwardly from the longitudinal sides of the garment 10 and preferably converge generally toward the center of the crotch portion 12 to form an inverted, but truncated, triangular shape adjacent the area where the back portion 16 joins the crotch portion 12. Attached to each of the longitudinal marginal edges of the back portion 16 are one or more garment securing means 18, which will be described more particularly hereinafter.

In its preferred construction, the disposable garment 10 includes a fluid pervious or porous inner (body-facing) cover sheet 20, a fluid impervious outer sheet 22 and an absorbent layer or batt of material 24 interposed therebetween. For purposes of clarity, portions of the inner cover sheet 20 and absorbent batt 24 have been broken away in FIG. 1 to better illustrate the underlaying layers and components of the garment 10. Desirably, the absorbent batt 24 generally conforms to the "Block I" or hour-glass shape of the inner cover sheet 20 and outer cover sheet 22, but the batt 24 is somewhat smaller in its overall dimensions so that the inner and outer cover sheets 20 and 22 can be attached at the entire periphery but outside the periphery of the absorbent batt 24, if desired. Such attachment may be accomplished, for example, by adhesives or thermal or ultrasonic bonding methods, all of which are known in the art.

In order to stabilize the garment 10 and enhance the internal integrity thereof, the absorbent batt 24 is desirably adhered to either the inner cover sheet 20 or the outer cover sheet 22 or both. Preferably, the batt 24 is bonded to the outer cover sheet 22 by a plurality of longitudinally extending lines of adhesive 26 (only a few of which are shown) that also bond the marginal edges of the inner and outer cover sheets 20 and 22 together. Other methods of securing the absorbent batt 24 and the inner and outer cover sheets 20 and 22 together may also be employed.

Typically, the impervious outer cover sheet 22 may be formed of a olefinic or vinyl plastic, such as polyethylene of about 0.5 to 1.5 mil thickness, although other impervious materials may also be used. The fluid pervious inner cover sheet 20 is preferably a nonwoven material such as a bonded carded web of fibers (synthetic and/or natural) or a spunbonded web of continuous filaments, for example, randomly laid polypropylene filaments bonded together with heat and pressure. The absorbent batt 24 may be formed of wood pulp fluff, plies of cellulose tissue, super absorbent materials, open cell foam elements or some combination thereof. In a preferred embodiment, the absorbent batt 24 is made of a mixture of a nonwoven spunbonded filaments simultaneously formed with wood pulp fluff. The resulting batt of absorbent material has enhanced integrity and rigidity as compared to fluff or tissue alone or as normally combined.

The absorbent batt 24 may have a uniform cross-sectional thickness but, in the preferred embodiment, the absorbent batt 24 is provided with increased thickness in the crotch portion 12 of the garment 10. This may be afforded by a separate pad of absorbent material interposed between the absorbent batt 24 and the outer cover sheet 22 or, more desirably as in the illustrated embodiments, the increased thickness may be formed by folding into the crotch portion 12 the lateral portions of the batt 24 which would otherwise be removed to form the leg cut-out areas of the garment.

Figure 2:
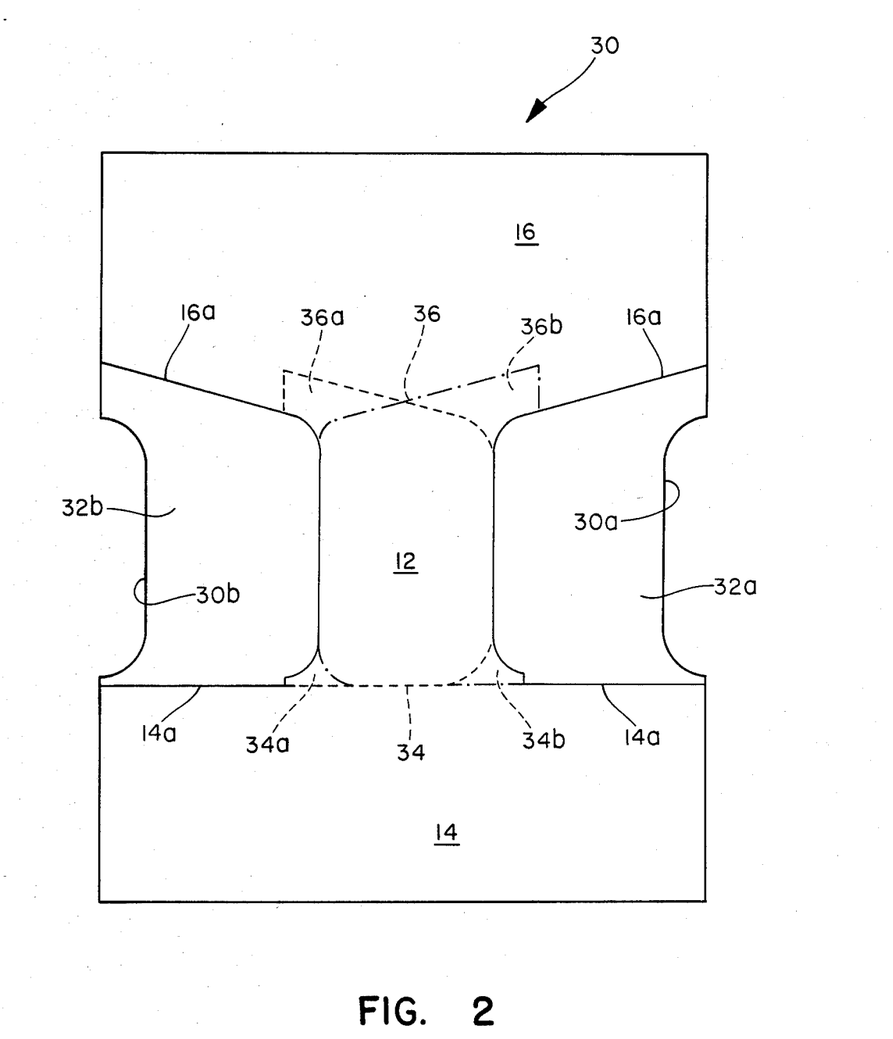
FIG. 2 is a top plan view of the absorbent batt of the garment of FIG. 1, showing: in solid lines the cut-out pad; and, in dot-dash lines the leg opening areas of the pad interfolded into the crotch portion of the pad.

Referring to FIG. 2, a generally rectangular sheet 30 of absorbent material is provided which is then cut and folded into the composite batt 24. As seen here, relatively narrow cut-outs 30a and b are removed from the sides of the sheet 30, but it should be understood that such cast-outs need not be removed but rather, if desired, may be folded into the crotch area. The sides of the sheet are also cut along lines 14a and 16a which extend from the side edges of the sheet 30 in toward the crotch portion 12 to form two side flaps 32a and 32b. These side flaps 32a and 32b are then folded in and under the central crotch portion 12 to form a three layer composite having a shape as generally outlined by the dash and dot-dash lines in FIGS. 1 and 2.

The front edge of the multi-layer absorbent batt 24 adjacent the front portion 14 is defined by a generally transverse portion 34 which terminates in lateral ears 34a and 34b. Similarly, the rear edge of the composite batt 24 adjacent the rear portion 16 is defined by a shallow V-shaped portion 36 which terminates in a pair of lateral ears 36a and 36b just outboard of the crotch portion 12.

Figure 2A:
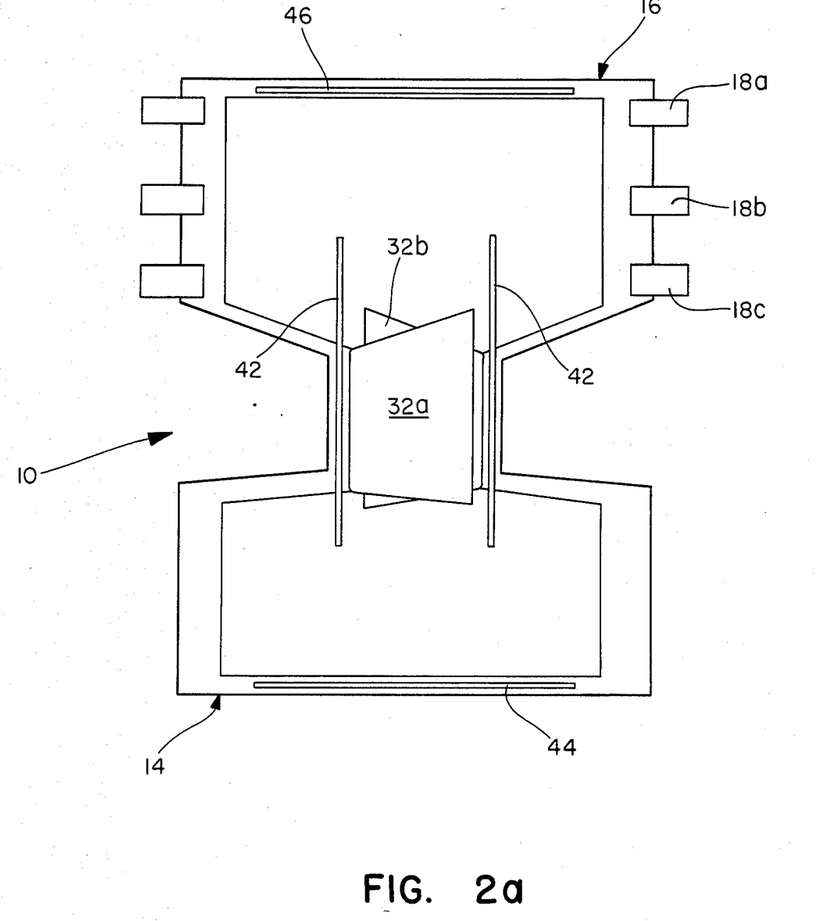

An alternative embodiment is shown in FIG. 2a. As will be seen from the drawing, the side flaps 32a and 32b are cut from a somewhat different dimensioned sheet 30 and folded into the crotch portion to form a three layer composite having the configuration as shown.

To further insure a leak-proof, yet comfortable, fit of the garment 10 about the legs of the wearer, the crotch portion 12 is provided with a pair of laterally spaced, longitudinally extending elastic leg bands 42. Preferably, the elastic bands 42 are disposed generally parallel (although they could be somewhat arcuate) outboard of the edges of the necked-down absorbent batt 24 but within the periphery of the crotch portion of the hourglass shaped inner and outer cover sheets 20 and 22. In this area, the elastic leg bands 42 are affixed or adhered directly to either the inner or outer sheets 20, 22 either intermittently or continuously, or are confined therebetween by the bonding medium used to attach these sheets together, thereby providing anchored extremities 42a. The elastic leg bands 42 extend longitudinally out from the crotch portion 12 and into the front portion 14 and rear portion 16 of the garment. The reason for extending the elastic leg bands into the ears is to improve the fit of the garment to the body. The garment is more form-fitting to the buttocks thereby minimizing a droopy effect.

In accordance with the present invention, the incontinence garment 10 is also provided with a front elastic waist band 44 and a back elastic waist band 46 which, respectively, extend transversely at least partially across the front portion 14 and rear portion 16 adjacent their latitudinal marginal edges which are transverse relative to the longitudinal edges. Preferably, the elastic waist bands 44, 46 are disposed outboard of the T-shaped ends of the absorbent batt 24 but within the periphery of the inner and outer cover sheets 20 and 22. The elastic waist bands 44, 46 are affixed or adhered by any suitable bonding technique either intermittently or continuously to one of the inner and outer cover sheets 20 and 22 or simply confined therebetween, thereby providing anchored extremities 44a and 46a.

The elastic bands 42, 44 and 46 may be formed of any suitable elastomeric material such as natural or synthetic rubber, elastomeric plastic materials or the like and may be applied in prestretched strip form (bands, ribbons, threads or the like) or may be directly extruded onto the sheet material and allowed to "set-up" in situ. In any event, the elastic bands 42, 44 and 46 should have an extension of at least about 2:1 and more preferably about 3:1 or 4:1 from their relaxed length before being applied to the sheet material.

It will be appreciated that each of the elastic leg bands 42 sets up an elastically contractable line of force along the respective longitudinally margins or side edges of the crotch portion 12 to help gather the absorbent batt 24 and the peripheral leg areas of the inner cover sheet 20 and outer cover sheet 22 snugly around the inner leg portions or thighs of the wearer. These longitudinal contracting lines of force are indicated by the arrows C in FIG. 3 and extend generally between the anchored ends 42a of the leg elastic bands 42. Somewhat similarly, the elastic waist bands 44, 46 establish elastically contractable lines of force, as indicated by the arrows D and E, which extend between the anchored ends 44a and 46a respectively, in FIG. 3, adjacent the ends of the front and back portions 14, 16 of the garment 10.

Figure 3:
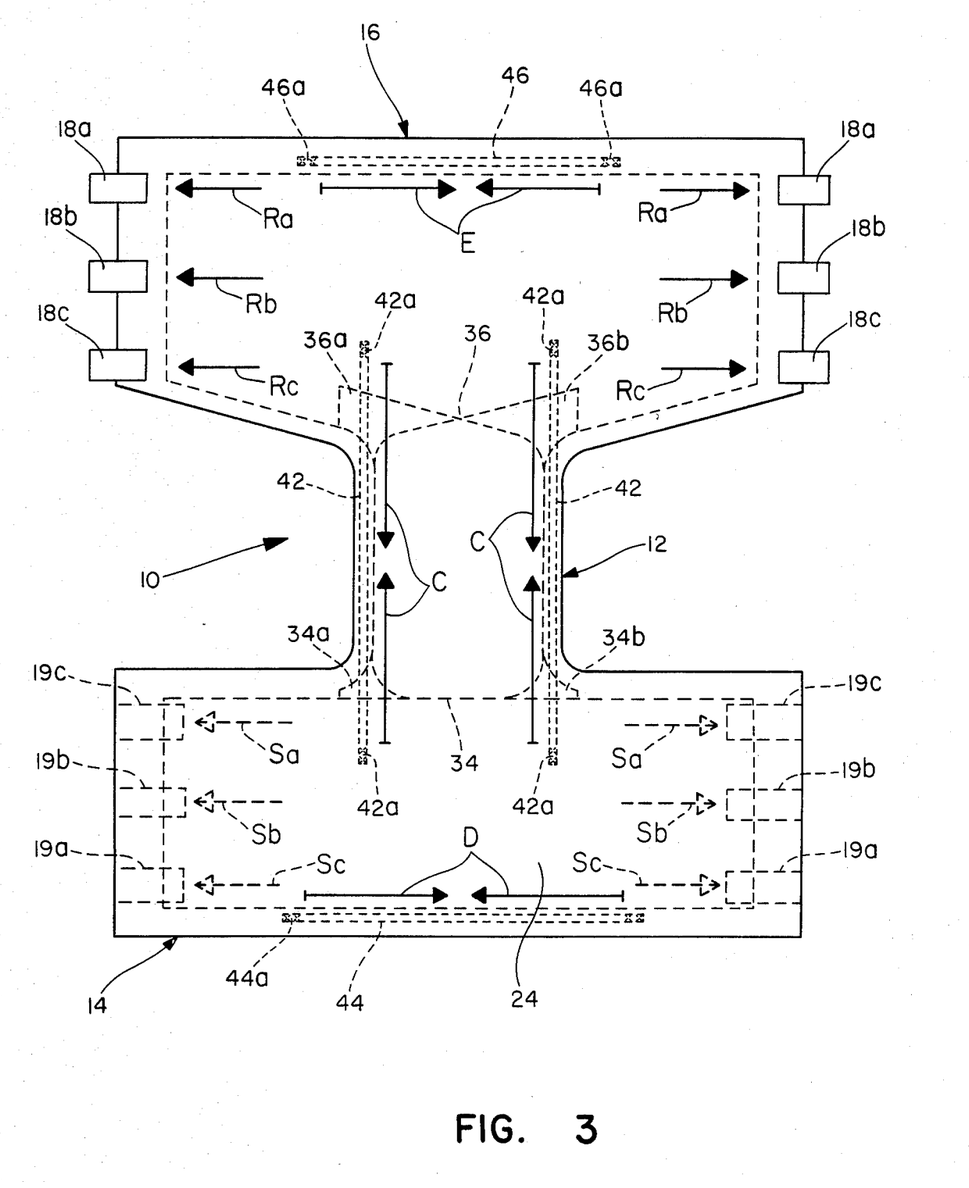
FIG. 3 is a plan view similar to FIG. 1 showing the lines of contracting force and attachment tape tab resistance.

In the illustrated embodiment the garment securement means, indicated generally at 18, preferably comprises a plurality of attachment tapes 18a, 18b and 18c applied to the outer sheet 22 at spaced locations along the longitudinal edges of the back portion 16 of the garment 10. These tapes are generally similar to those in use on conventional disposable diapers and are typically unfolded from a release coated portion on the inner cover sheet 20 and then reapplied to the outer cover sheet 22 of the front portion 14 in the general areas indicated by dash lines at 19a, 19b and 19c, respectively, in FIG. 3. It will be appreciated, of course, that the securement tapes 18a, b and c and their associated attachment areas 19a, b and c establish lines of resistance, as indicated in FIG. 3 by the arrows Ra, Rb and Rc, and Sa, Sb and Sc, which oppose the lateral waist band contracting forces D and E respectively, and also the longitudinal leg band contracting forces C.

Figure 4:
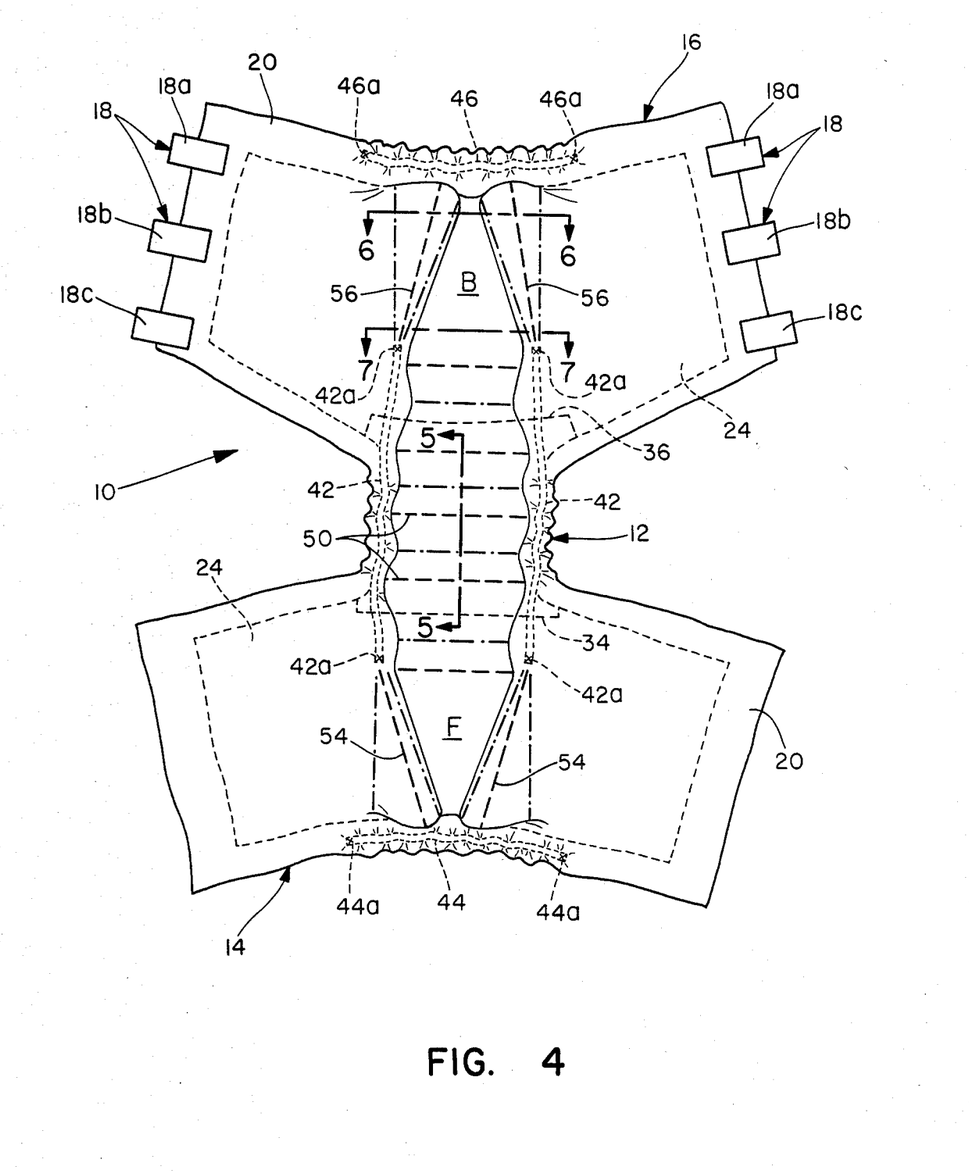
FIG. 4 is a plan view similar to FIG. 1 but with the garment relaxed (i.e., contracted) showing the convolutions in the crotch portion and the pleats and pockets in the front and back portions of the garment.
Figure 5:
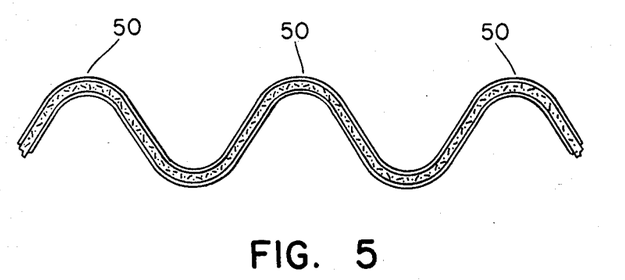
FIGS. 5, 6 and 7 are enlarged fragmentary section taken generally as seen along lines 5—5, 6—6, and 7—7 in FIG. 4, respectively; and, FIG. 8 is a frontal view of the disposable incontinence garment of the present invention as worn by a user.

Turning now to FIG. 4, it will be seen that the elastic leg bands 42 serve to longitudinally contract the central crotch portion 12 of the garment 10 and thereby form a plurality of large convolutions 50 (alternating ridges indicated by dash lines and valleys indicated by dot-dash lines) which extend generally transversely across the crotch 12 of the garment 10. (See also FIG. 5.) The formation of these transverse convolutions 50 tends to concentrate the absorbent material of the batt 24 in the area where it is most needed to absorb fluid discharges.

Figure 6:
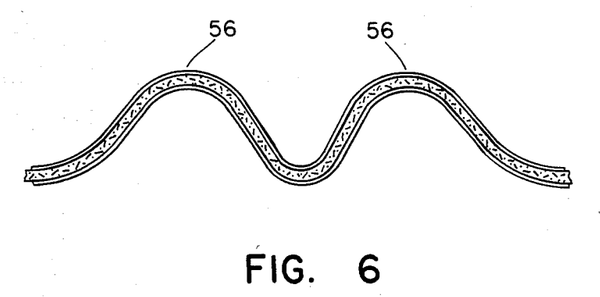
Figure 7:
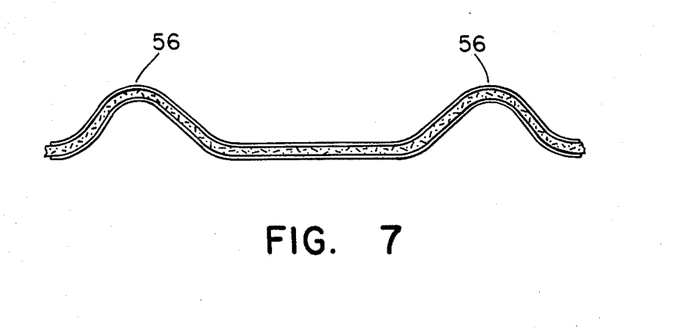

The elastic waist bands 44 and 46 likewise serve to contract the marginal ends or waist portions of the front and back body-encircling portions 14 and 16 of the garment 10 and form at least a pair of large longitudinally angled convolutions designated generally at 54 and 56, respectively, in FIGS. 4, 6 and 7. Although there may be some gathering or pleating of the areas of the front and back portions 14, 16 outboard of the large convolutions 54 and 56, these outboard end areas are generally flat and smooth. In any event, when the garment is applied and the back portion 16 is pulled around the body of the wearer and attached to the front portion 14 by the securing means 18, the resisting forces R and S tend to pull out any minor ripples in the outboard areas of the portions 14 and 16. (See also FIG. 8.)

Pursuant to the present invention, the ends 42a, 44a and 46a of the elastic bands 42, 44 and 46 are anchored in the front and rear portions 14 and 16 of the garment 10 at locations which, due to the interaction of the elastic bands and sheet materials, form generally triangular front and back pocket portions in the garment as indicated generally at F and B in FIG. 4. Typically, the front triangular pocket F is defined along its legs by the large longitudinally angled convolutions 54 and along its base by the forward most one of the transverse convolutions 50. Similarly, the back triangular pocket B is generally defined along its legs by the large longitudinally angled convolutions 56 and along its base by the rearwardmost one of the transverse convolutions 50. While there may be some gathering, pleating or other irregularities formed in the front and rear pockets F and B, these pocket areas are essentially flat and smooth.

In the preferred embodiment, the elastic leg bands 42 extend into the front and rear portions 14 and 16 approximately 30% to 60% of the longitudinal distance from the ends of the crotch portion 12, as defined by the intersection of the elastic leg bands with the batt 24, to the front and rear elastic waist bands 44 and 46, respectively. Also as seen in FIGS. 1 and 3, the elastic leg bands 42 are disposed longitudinally within the lengths of the elastic waist bands 44 and 46 between the anchored ends 44a and 46a thereof. Preferably the elastic waist bands 44 and 46 are generally centered near the edges of the respective front and back portions 14 and 16 and when fully stretched extend transversely partially across the width thereof from about 55% to 75% of the total width of the portions 14 and 16. The location of the elastic bands 42, 44 and 46 and their respective anchor points within the front and back portions 14 and 16 are instrumental in forming the front and back pockets F and B of the illustrative garment 10.

Figure 8:
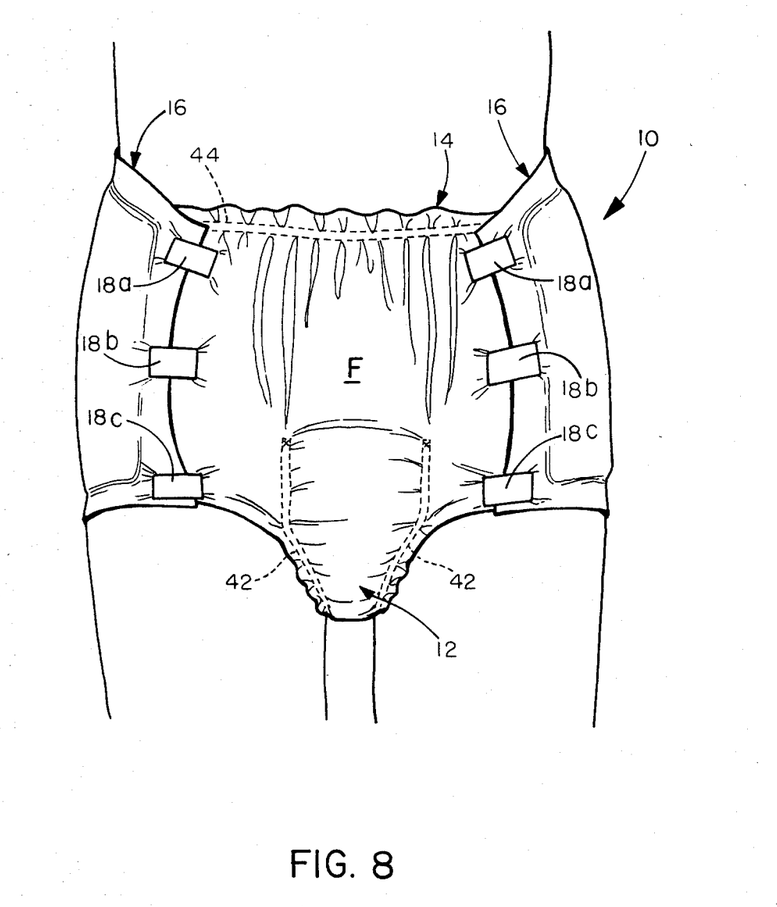

It will be appreciated that the rear or back pocket B provides an expandable pouch-like area which facilitates the containment of excrement. The front pocket F also provides an expandable pouch-like area in the lower front portion of the garment which is particularly desirable for adult male users of the garment 10 without seriously diminishing the sealing action afforded by the elasticized leg and waist band areas. A front view of the garment as worn by a user is shown in FIG. 8. Additionally, the elastic waist bands 44 and 46 permit the user to pull the front portion 14 or back portion 16 of the garment 10 away from the body to determine if it is wet or solied and the garment 10 may also be slipped down on the legs of the wearer to permit normal use of a toilet when desired.

Because the front and rear elastic waist bands 44 and 46 are partially extended (i.e. stretched) during use, they are generally taut relative to their fully contracted or relaxed condition. As a result, the elastic waist bands 44 and 46 provide an uplifting action to not only prevent sagging of the front and rear body-encircling portions 14 and 16, but also, to help support front and back pocket areas F and B, respectively. This affords a snug-fitting garment 10 with good sealing action around the thighs and waist of the user and also the formation of the generally triangular front and rear pockets F and B enhance the containment capabilities of the garment 10 and its comfort to the user.

From the foregoing, it will be seen that the disposable garment 10, employing the features of the present invention, is well suited for use as an incontinent brief or adult diaper and possesses improved features of snugness of fit, sealing and security as well a superior attributes of containment, convenience and comfort.

I claim as my invention:

1. In a disposable garment having a fluid pervious inner sheet, a fluid impervious outer sheet and a batt of absorbent material therebetween and having a generally hour-glass shape with a narrow crotch portion integral to oppositely disposed front and back body-encircling portions, at least one of the latter having garment securement means attached to the side edges thereof, and including elastic leg bands disposed longitudinally adjacent the longitudinal margins of the crotch portion and extending into the front and back portions of the garment and with elastic waist bands transversely extending across said front and back portions adjacent the latitudinal margins thereof, the improvement comprising:

elastic waist bands affixed to at least one of said inner and outer sheets in said front and back portions outboard of longitudinal lines extending generally along the longitudinal margins of said crotch portion, elastic leg bands affixed to at least one of said inner and outer sheets in said front and back portions between the crotch portion and said elastic waist bands and inboard of the anchored ends of the later, said elastic leg bands exerting a longitudinal contracting and convoluting force in the crotch portion of the garment, said elastic waist bands exerting a transverse contracting and convoluting force adjacent the latitudinal margins of said front and back body-encircling portions, and the contraction of said elastic leg bands and waist bands interacting to form generally truncated triangular front and back pocket portions having one or more large longitudinally angled convolutions forming the legs of said triangles and with the bases of said triangular portions located generally along the margins of said contracted and convoluted crotch portion of the garment.

2. A disposable garment as defined in claim 1 wherein said securement means includes a plurality of adhesive tapes attached to said back body-encircling portion with an upper tape on each side thereof extending laterally outward therefrom generally along and adjacent to an extension of the lines of contracting force exerted by said back waist band elastic.

3. A disposable garment as defined in claim 2 wherein said securement means includes upper and lower tapes on each side of said back portion with an intermediate tape disposed therebetween.

4. A disposable garment as defined in claim 1 wherein said securement means includes a plurality of adhesive tapes attached to said back body-encircling portion with a lower tape on each side thereof extending laterally outward therefrom generally adjacent to or below a transverse line extending from the affixed extremities of said elastic leg bands located in said back portion.

5. A disposable garment as defined in claim 4 wherein said securement means includes upper and lower tapes on each side of said back portion with an intermediate tape disposed therebetween.

6. A disposable garment as defined in claim 2 wherein said upper securement tapes, when attached to the garment in use, resist the transverse contracting force adjacent the ends of said front and back body-encircling portions and thus provide upward support for said front and back pocket portions.

7. A disposable garment as defined in claim 4 wherein said lower securement tapes, when attached to the garment in use, resist the longitudinal contracting force exerted by said elastic leg bands and thus provide a snug fit and seal of the crotch portion of the garment to thighs of the user.

8. A disposable garment as defined in claim 3 wherein said intermediate securement tapes, when attached to the garment in use, are effective to close the central areas of the side margins of said front and back portion's and also stabilize the mid portions of the convoluted legs of said triangular portions.

9. A disposable garment as defined in claim 5 wherein said intermediate securement tapes, when attached to the garment in use, are effective to close the central areas of the side margins of said front and back portions and also stabilize the mid portions of the convoluted legs of said triangular portions.

10. A disposable garment as defined in claim 1 wherein said elastic leg bands extend into said front and rear portions of the garment about 30% to 60% of the distance from the ends of said crotch portion to said front and back elastic waist bands, respectively.

11. A disposable garment as defined in claim 1 wherein said elastic waist bands extend from about 55% to 70% of the width of said front and back portions.

12. A disposable garment as defined in claim 1 wherein said batt of absorbent material includes multiple layers in said crotch portion of the garment.

13. A disposable garment as defined in claim 12 wherein said batt of absorbent material is made from a generally rectangular sheet cut laterally inwardly along latitudinally spaced lines from the sides thereof toward the crotch to form a pair of side flaps which are interfolded in and under the crotch portion of the sheet to form a composite multi-layer absorbent batt.

14. In a disposable garment having a fluid pervious inner sheet, a fluid impervious outer sheet and a batt of absorbent material therebetween and having a generally hour-glass shape with a narrow crotch portion integrally connected to oppositely disposed front and back body-encircling portions, at least one of the latter having garment securement means attached to the side edges thereof, and including elastic leg bands disposed longitudinally along the longitudinal marginal edges of the crotch portion and extending into the front and back portions of the garment and with at least one strip of elastic waist band transversely extending across at least one of said front and back portions adjacent the latitudinal margin thereof, the improvement comprising:

elastic waist bands affixed to at least one of said inner and outer sheets in said one of said front and back portions outboard of longitudinal lines extending generally along the longitudinal edges of said crotch portion, elastic leg bands affixed to at least one of said inner and outer sheets in said front and back portions between the crotch portion and the ends of said front and back portions, said elastic leg bands exerting a longitudinal contracting and convoluting force in the crotch portion of the garment, said elastic waist band exerting a transverse contracting and convoluting force adjacent the latitudinal margin of said one of said front and back body-encircling portions, and said elastic leg bands and said waist band interacting to form a generally truncated triangular pocket portion in said one of said front and back portions, said triangular pocket having one or more large longitudinally angled convolutions forming the legs of said triangular portion and with the base of said triangular portion located generally along the end of said contracted and convoluted crotch portion of the garment.

15. A disposable garment as defined in claim 14 wherein said elastic waist band is affixed to said back portion of the garment and said triangular pocket portion is formed generally with its base adjacent the rear of said crotch portion and said legs extend upwardly adjacent said elastic waist band in said back portion of the garment.

16. A disposable garment as defined in claim 14 wherein said elastic waist band is affixed to said front portion of the garment and said triangular pocket portion is formed generally with its base adjacent the front of said crotch portion and said legs extend upwardly adjacent said elastic waist band in said front portion of the garment.

17. A disposable garment as defined in claim 14 wherein said securement means includes a plurality of adhesive tapes attached to said back body-encircling portion with an upper tape on each side thereof extending laterally outward therefrom generally along and adjacent to an extension of the line of contracting force exerted by said back waist band elastic.

18. A disposable garment as defined in claim 17 wherein said securement means includes upper and lower tapes on each side of said back portion with an intermediate tape disposed therebetween.

19. A disposable garment as defined in claim 14 wherein said securement means includes a pluality of adhesive tapes attached to said back body-encircling portion with a lower tape on each side thereof extending laterally outward therefrom generally adjacent to or below a transverse line extending through the affixed extremities of said elastic leg bands located in said back portion.

20. A disposable garment as defined in claim 19 wherein said securement means includes upper and lower tapes on each side of said back portion with an intermediate tape disposed therebetween.

* * * * *